United States Patent [19]

Carter et al.

[11] Patent Number: 4,554,687
[45] Date of Patent: Nov. 26, 1985

[54] TOILET MOUNTED URINE FLOW METER

[75] Inventors: Garry L. Carter; Vaughan B. Weeks, both of Racine, Wis.

[73] Assignee: Medical Engineering Corporation, Racine, Wis.

[21] Appl. No.: 674,561

[22] Filed: Nov. 26, 1984

Related U.S. Application Data

[63] Continuation-in-part of Ser. No. 450,677, Dec. 17, 1982, abandoned.

[51] Int. Cl.[4] .......................... A47K 11/00; G01F 1/20
[52] U.S. Cl. ....................................... 4/144.2; 73/216; 4/144.1; 4/451; 4/463; 128/760
[58] Field of Search .................... 128/760, 761; 4/462, 4/463, 481, 661, 144.1, 144.2, 144.4, 451; 73/861, 198, 216, 215, 223; 141/339

[56] References Cited

U.S. PATENT DOCUMENTS

| | | | |
|---|---|---|---|
| Re. 30,607 | 5/1981 | Manschot et al. | 128/762 |
| 1,662,147 | 3/1928 | Farden | 141/339 |
| 2,174,228 | 9/1939 | Perkins | 141/339 |
| 2,562,816 | 7/1951 | Painter | 4/481 |
| 3,654,638 | 4/1972 | Nye | 4/110 |
| 3,726,140 | 4/1973 | Barbee | 73/299 |
| 3,919,455 | 11/1975 | Sigdell et al. | 73/226 |
| 3,986,398 | 10/1976 | Laymance | 73/299 |
| 4,000,649 | 1/1977 | Hanifl | 73/219 |
| 4,020,690 | 5/1977 | Samuels et al. | 73/299 |
| 4,051,431 | 9/1977 | Wurster | 324/61 R |
| 4,084,435 | 4/1978 | Weik et al. | 73/299 |
| 4,085,616 | 4/1978 | Patel et al. | 73/215 |
| 4,099,412 | 7/1978 | Nehrbass | 73/209 |
| 4,137,573 | 2/1979 | Kroeger | 4/144.1 |
| 4,187,722 | 2/1980 | Layton | 73/229 |
| 4,200,112 | 4/1980 | McWhorter | 128/761 |
| 4,203,169 | 5/1980 | Dale | 4/144.1 |
| 4,241,017 | 12/1980 | Balistreri et al. | 422/58 |
| 4,252,132 | 2/1981 | Kuntz | 128/761 |
| 4,301,813 | 11/1981 | Merry et al. | 128/762 |
| 4,343,316 | 8/1982 | Jesperson | 128/771 |

OTHER PUBLICATIONS

"Analysis of Micturition, A New Method of Recording the Voiding of the Bladder", *Acta Chirugica Scandinavica*, (1956) Von Garrelts, B., pp. 326–340.
"Uroflometry in Urological Diagnosis," Joseph J. Kaufman, *California Medicine*, vol. 95, Aug. 1961, pp. 100–103.
"A New Uroflowmeter for Routine Clinical Use," *Biomedical Engineering*, vol. 10, No. 1 (Jan. 1975), Randall, pp. 21–24.

*Primary Examiner*—James L. Rowland
*Assistant Examiner*—Brian R. Tumm
*Attorney, Agent, or Firm*—Quarles & Brady

[57] ABSTRACT

A urine flow meter including a toilet mounted collector is disclosed. The collector has a mouth portion which is dimensioned to fit within a toilet bowl and which has walls which slope downwardly and inwardly to a neck portion. The neck portion extends downwardly from the lower end of the mouth portion to receive urine directed into it from the mouth portion. An aperture is formed in the neck portion and a pressure sender has a lower end in communication with the neck portion. An upper end of the pressure sender is above the neck portion and is connected to a pressure transducer. Urine accumulates in the neck portion until the flow rate into the collector equals the flow rate out through the aperture. The accumulated volume of urine in the neck portion produces an air pressure within the pressure sender which is converted into an electrical signal by the pressure transducer. The pressure transducer output signal is suitable to be processed to provide critical urine flow data.

4 Claims, 6 Drawing Figures

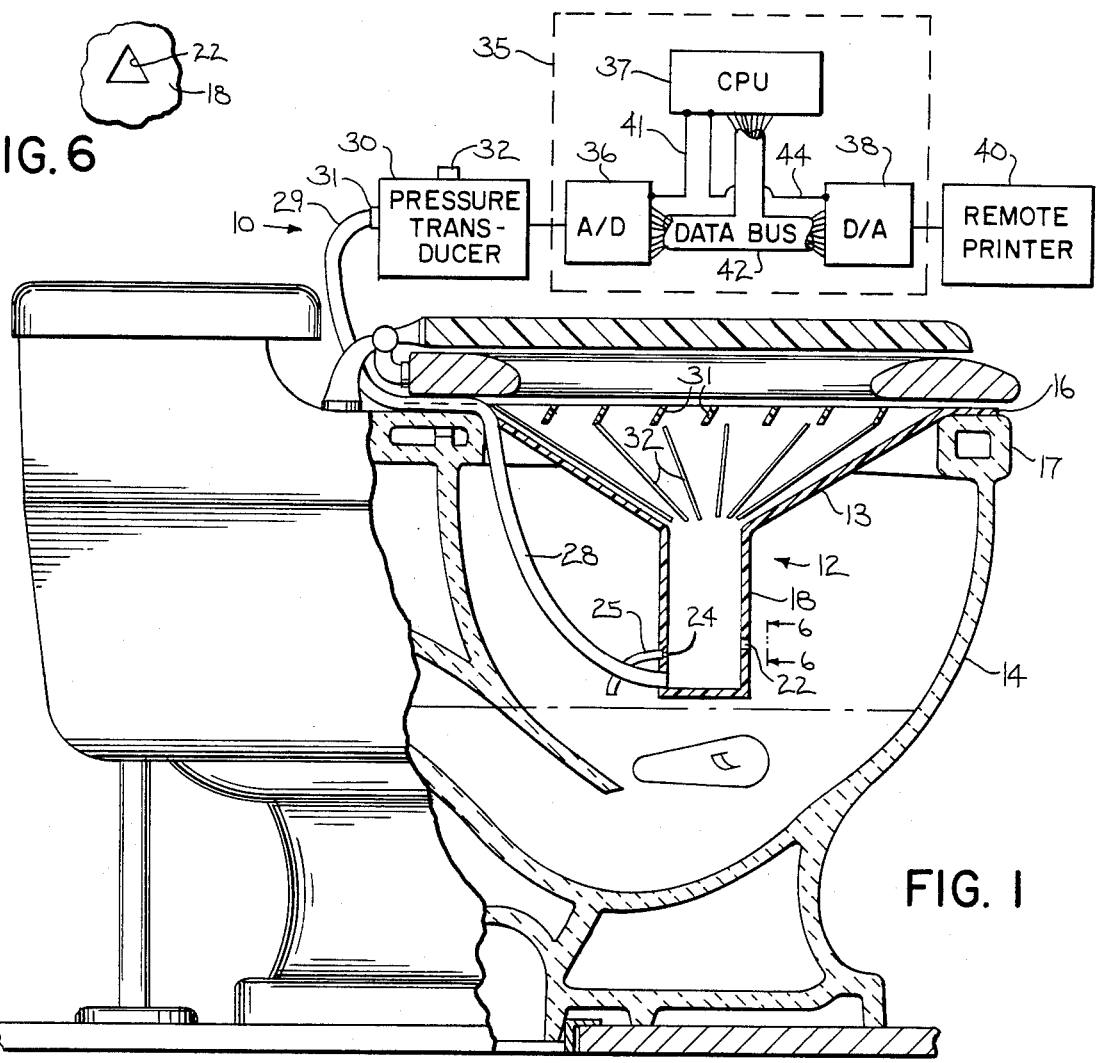
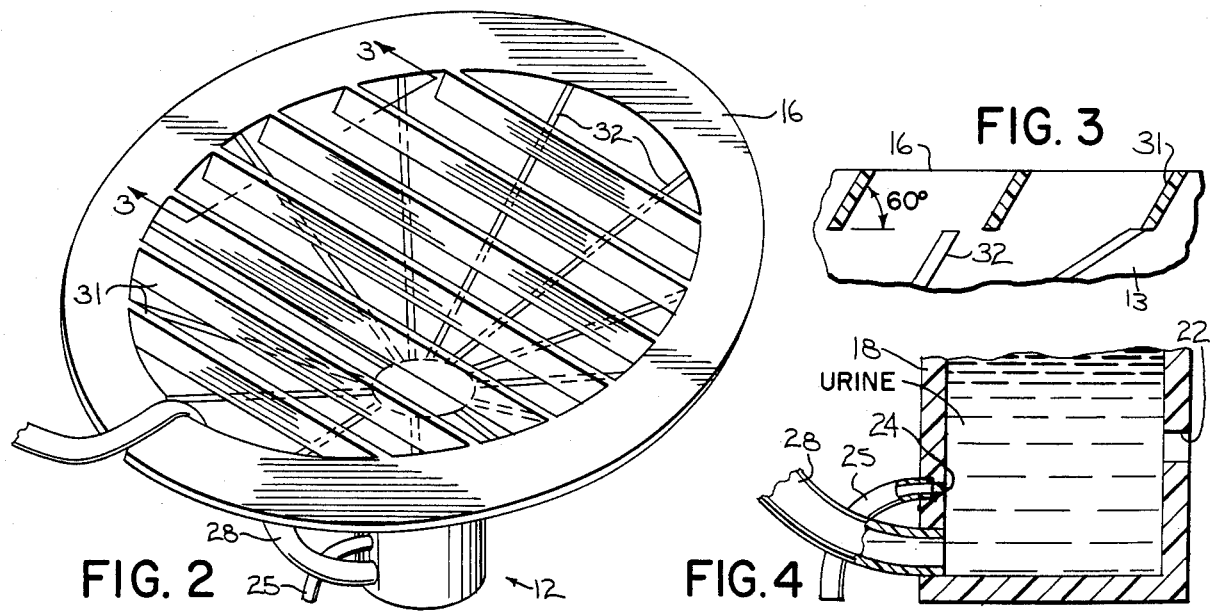

TOILET MOUNTED URINE FLOW METER

This is a continuation-in-part of application Ser. No. 450,677, filed Dec. 17, 1982, now abandoned.

FIELD OF THE INVENTION

This invention relates to urine flow meters and particularly to a urine flow meter having a toilet mounted collector.

BACKGROUND OF THE INVENTION

Diagnosis of urological disorders is often facilitated by a patient's urine flow rate data. Urological disorders such as an obstruction in the lower urological tract or neurotic bladder can be detected by studying the patient's urine flow rate as it varies from the beginning of voiding to the end and the total volume of urine voided. This data can be compared to the mean data for an individual of the same sex and age to help determine the degree of urethral stricture.

Urine flow data is also useful in diagnosing prostrate enlargement. Prostrate enlargement usually occurs gradually with no noticeable impairment to the patient. Merely observing the patient void will usually not enable the urologist or physician to accurately assess the degree of prostate enlargement. However, by observing histograms of the urine flow, the urologist or physician can usually detect the degree of prostrate enlargement and the necessary procedures to be undertaken to correct the disorder. In addition, post-operative urine flow data provides an excellent way of assessing the benefit achieved by surgery.

Several different types of urine flow meters for providing urine flow data are presently commercially available. Examples of a mechanical urine flow meter for enabling manual measurement of urine flow are found in U.S. Pat. Nos. 4,099,412, 4,200,112, 4,241,017, 4,000,649, 4,085,616, 4,301,813 and reissue patent 30,607. These mechanical urine flow measuring devices usually comprise a container having a graduated scale for indicating the volume of urine within the container. Urine flow is detected by manually observing the change in volume as the patient voids into the container. These devices therefore require that either a physician, a nurse or a technician observe the patient void into the container. While a privacy screen is usually provided between the patient and the observer, the patient may still exhibit distress or embarassment knowing that his or her voided stream is being observed.

To overcome this disadvantage, electrical urine flow meters for providing urine flow data have been developed. For example, U.S. Pat. No. 4,187,722 discloses a urine velocity measuring device including a urine flow receptacle having a paddle wheel journaled therein. The paddle wheel is mechanically linked to a generator which produces an output voltage which is displayed on a volt meter. The velocity of the urine stream impinging on the paddle wheel determines the paddle wheel velocity and therefore the output voltage of the generator.

U.S. Pat. No. 4,051,431 discloses another device for measuring a urine flow electrically. The urine flow meter disclosed in this patent includes a urine receiving receptacle which has a pair of parallel spaced-apart rods or strips disposed therein. The rods or strips are electrically connected to a capacitance sensing circuit. As the volume of urine within the receptacle increases, the capacitance between the rods also increases so that by measuring the rate of change of the capacitance, an indication of the urine flow may be obtained.

Both of the above described electrical urine flow meters require a high degree of maintenance. Since urine contacts components of each of the meters, those components must be cleaned following each use. Therefore, a need exists for a low maintenance electrical urine flow meter.

SUMMARY OF THE INVENTION

The invention provides a urine flow meter including a toilet mounted collector. The collector has a mouth portion which is dimensioned to fit within a toilet bowl and which has walls which slope downwardly and inwardly from an open upper end to an open lower end. A neck portion extends downwardly from the lower end of the mouth portion and has a substantially closed lower portion. An aperture is formed in the lower portion of the neck portion and a pressure sender is in communication with the lower portion of the neck portion. The end of the pressure sender opposite from the neck portion is above the neck portion and is suitable for connection to a pressure transducer. The mouth portion directs urine into the neck portion where the urine accumulates. The accumulated volume of urine in the neck portion produces an air pressure within the pressure sender which is suitable to be processed to provide critical urine flow data. The aperture allows the urine to exit to the toilet bowl at a rate which is dependent upon the volume of urine in the neck portion.

A pressure transducer is connected to the upper end of the pressure sender and provides an electrical signal which is proportional to the air pressure within the pressure sender. A processor is connected to the pressure transducer for converting the pressure transducer output signal into a flow rate signal. The flow rate signal can be further manipulated and/or output means provided for displaying the resulting data.

The invention provides an improved urine flow meter which enables accurate urine flow rate measurement. Much of the anxiety that a patient may have had with prior art mechanical urine flow meters is relieved because the urine collector of the invention is mounted within a toilet. This not only obviates the need for an observer of the voiding process, but simulates natural voiding since it is mounted in a toilet.

The invention also provides a urine flow meter which is easy to maintain. A collector for a urine flow meter of the invention can be inexpensively manufactured from suitable plastic materials since it has no moving or electrically conductive parts. Since it is inexpensive, it can be disposed after each use thereby alleviating the cleaning difficulties associated with prior art flow meters.

Other objects and advantages of the present invention will become apparent from the following detailed description and drawings.

DESCRIPTION OF THE DRAWINGS

FIG. 1 is a side plan view of a urine flow meter constructed in accordance with the present invention;

FIG. 2 is a perspective view of a toilet mounted collector for the urine flow meter of FIG. 1;

FIG. 3 is a sectional view taken along the plane of line 3—3 of FIG. 2;

FIG. 4 is a detail view partially in section of the lower portion of the collector of FIG. 2;

FIG. 6 is a view taken along the plane of line 6—6 of FIG. 1.

DETAILED DESCRIPTION OF THE PREFERRED EMBODIMENT

Figure 5:
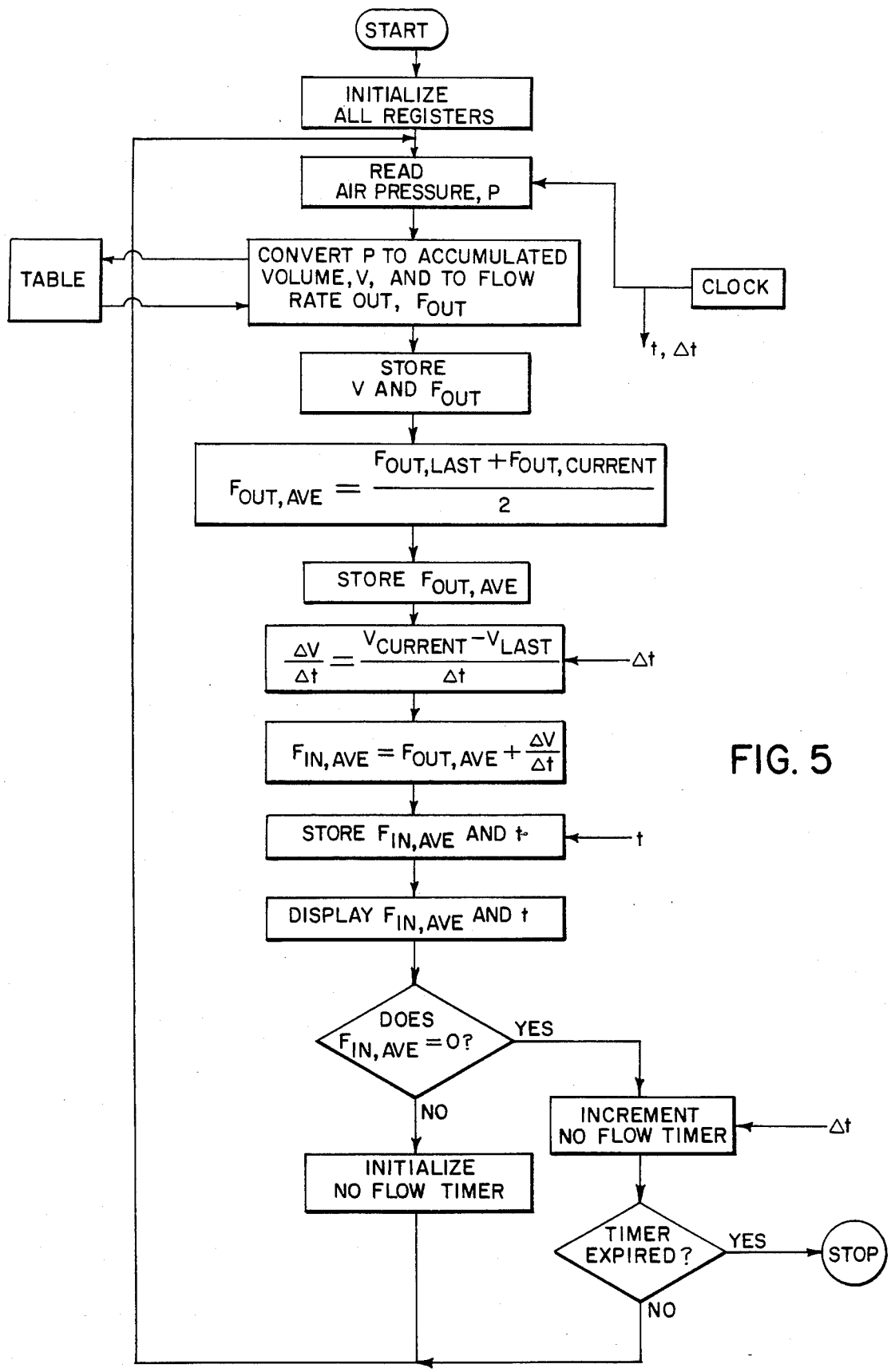
FIG. 5 is a flow chart for the processor of FIG. 1.

Referring to FIG. 1, a urine flow meter 10 of the present invention includes a collector 12. The collector 12 has a funnel shaped mouth portion 13 which is dimensioned to fit within a toilet bowl 14. The mouth portion 13 has walls which slope downwardly and inwardly from an open upper end to an open lower end. While the mouth portion 13 shown is frusto-conically shaped, any mouth portion with walls which slope downwardly and inwardly could be employed in the collector 12. A flange 16 circumscribes the periphery of the upper end of the mouth portion 13 so that the collector may be supported by a rim 17 of the toilet bowl 14. Alternatively, a separate frame (not shown) could be employed to support the collector 12 within the toilet bowl 14.

A circular cylindrical neck portion 18 extends downwardly from the lower end of the mouth portion 13. The lower end of the neck portion 18 is closed and the lower portion of the neck portion is provided with a triangular-shaped aperture 22 (FIG. 6). A bleeder aperture 24 which is much smaller than the aperture 22 is located slightly below the level of the aperture 22 and is in communication with one end of a short downwardly depending tube 25. A pressure sender 28, which may be nothing more than an air filled tube, is in communication with the lower portion of the neck 18 preferably below the levels of the apertures 22 and 24. The pressure sender 28 extends upwardly above the neck portion 18 and has an end 29 which is suitable to be connected to a pressure transducer 30.

While the preferred embodiment disclosed has two apertures 22 and 24, it is not necessary that two apertures be provided to practice the invention. The reason that the aperture 24 is provided is to allow a very small amount of urine to exit therethrough to reduce the surface level of the urine in the neck 14 to being below the level of the aperture 22. Surface tension effects at the level of the aperture 22 can cause somewhat erratic flow rate measurements. To alleviate these effects, the aperture 24 is positioned below the aperture 22, is much smaller than the aperture 22 and is provided with the downwardly depending tube 25. The tube 25 draws the level of the urine within the neck 18 down by siphon action to below the level of the aperture 22 upon the cessation of flow into the collector 12 to alleviate these surface tension effects. However, in some circumstances, these surface tension effects may not be apparent or may be negligible so that a bleeder aperture 24 is not necessary.

Also, the aperture 22 need not be triangular. Depending upon the application, it could be almost any shape. The preferred embodiment employs a triangular shaped aperture 22 merely because that shape was found satisfactory in practice. Similarly, the neck portion 18 need not be circular cylindrical.

The mouth portion 13 is provided as an easy target for a person voiding. A number of louvers 31 extend across the upper end of the mouth portion 13 as best illustrated in FIGS. 2 and 3. The louvers 31 are at an angle of about 60° with the flat surface of the flange 16 and serve to prevent urine from splashing out of the mouth portion 13 as a patient voids into the collector. The mouth portion 13 is also provided with a number of ridges 32 which extend radially inwardly along the conical walls of the mouth portion 13. The ridges 32 prevent the urine from swirling within the mouth portion 13 to prevent any centrifugal effects upon the level of urine in the neck portion 18.

Urine entering the mouth portion 13 is directed down into the neck portion 18 and accumulates therein. The combined areas of the apertures 22 and 24 are such that a typical urine flow causes the level of urine within the neck portion 18 to rise even after the level has surpassed the levels of the apertures 22 and 24. This is the case even though some of the urine will exit the apertures 22 and 24. The instantaneous flow rate out the apertures 22 and 24 will be determined by the instantaneous height of urine within the neck portion 18. This is because a certain height of urine within the neck portion 18 will produce a certain pressure at the level of each aperture 22 and 24. As the height of urine within the neck portion 18 increases, so does the pressure at the level of each aperture. This pressure increase causes the flow rate out each aperture to increase. When the height of urine has reached a level which causes the combined flow rates out the apertures 22 and 24 to equal the patient's urine flow rate into the collector 12, the level will stop rising and will remain constant at a steady state level. As noted, when the level of urine within the neck portion 18 is at a steady state level, the flow rate into the collector 12 equals the flow rate out.

The relationship between the flow rate in, the flow rate out, and the accumulated volume within the collector 12 is determined from a simple mass balance. Specifically, this relationship is that the flow rate in equals the flow rate out plus the rate of change of the accumulated volume of urine within the collector 12. Symbolically, this relationship is represented as follows:

$$\text{Flow}_{in} = \text{Flow}_{out} + (\Delta V / \Delta t),$$

where $\text{Flow}_{in}$ is the patient's average urine flow rate into the collector 12 over a time interval from $t_1$ to $t_2$, $\text{Flow}_{out}$ is the average flow rate out of the collector 12 over the same interval, $\Delta V$ is the change in volume of accumulated urine within the collector 12 from $t_1$ to $t_2$, and $\Delta t$ is the time interval which equals $t_2$ minus $t_1$.

With the pressure transducer 30 sealed over the end 29 of the pressure sender 28, some of the urine accumulating in the neck 18 will enter the sender 28 and will compress the air therein to cause the air pressure within the sender 28 to rise. The instantaneous pressure within the sender 28 will be determined by the instantaneous height of urine within the neck portion 18. Also, any given height of urine within the neck portion 18 will be associated with a certain volume of accumulated urine within the collector 12 including the volume within the neck portion 18 and the relatively small volume within the pressure sender 28. Note that since a certain height within the neck portion 18 is associated with a certain air pressure within the sender 28, a certain accumulated volume within the collector 12, and with a certain flow rate out of the collector 12, a given air pressure within the pressure sender 28 can be directly associated with a certain volume of accumulated urine in the collector 12 and with a certain flow rate out the collector 12 to determine the flow rate into the collector 12.

The pressure within the pressure sender 28 which is associated with a certain accumulated volume within the collector 12 and with a certain flow rate out of the collector 12 can be determined either experimentally or analytically. However, since the air in the pressure sender 28 is a compressible fluid, the analytical equation relating the air pressure to the accumulated volume of urine in the collector 12 and to the flow rate out of the collector 12 is somewhat complicated. On the other hand, the air pressures associated with various accumulated volumes of urine and flow rates out can be easily determined experimentally.

To associate air pressures within the sender 28 with accumulated volumes of urine within the collector 12 and with urine flow rates out of the collector 12, a known flow rate of urine or liquid with a comparable density would be introduced into the mouth portion 13. When the height of accumulated urine within the neck portion 18 reached the steady state level, the accumulated volume in the collector 12 and air pressure within the pressure sender 28 would be measured and recorded in a table to correlate them with the known flow rate. This procedure could be repeated for many different known flow rates into the neck portion 18 to provide a table of associated accumulated volumes, pressures and flow rates. Since the flow rate into the collector 12 equals the flow rate out when the urine in the neck portion 18 is at the steady state level, the table can be used to associate an instantaneous pressure within the pressure sender 28 with a certain accumulated volume of urine within the collector 12 and with a certain flow rate out of the collector 12 at the same instant in time regardless of whether the accumulated urine is at a steady state level.

The pressure transducer 30 provides an electrical signal in accordance with the air pressure in the pressure sender 28. The transducer 30 should be capable of following the air pressure within the sender 28 to provide an instantaneous indication thereof. Either gauge or absolute pressure can be sensed by the pressure transducer 30. However, it is preferable for the transducer 30 to sense gauge pressure. This is because atmospheric pressure acts on the urine in the neck 18 so that gauge pressure, which is the difference between the pressure in the sender 28 and atmospheric pressure, is a truer indication of the pressure attributable to the height of urine within the neck 18. If absolute pressure were sensed, the atmospheric pressure would have to be separately measured and subtracted from the absolute pressure to yield the pressure attributable to the height of urine in the neck 18.

A transducer 30 which was found suitable in practice is the transducer sold under the trade designation Microswitch #142PC01G. This transducer has a measuring port 31 and a gauge port 32. To measure gauge pressure, the measuring port 31 is connected to the end 29 of the sender 28 and the gauge port 32 is left open to the atmosphere.

The output signal of the transducer 30 could be displayed and compared to the table to determine the flow rate out of the collector 12 and the volume within the collector 12 at times $t_1$ and $t_2$. The mass balance explained above could then be applied to determine the average flow rate into the collector 12 over the time interval from $t_1$ to $t_2$. This could be done for a number of time intervals and the resulting flow rates plotted to yield a histogram of the flow rate. The histogram could then be studied to yield valuable information about the urine flow, or it could be further manipulated to yield other data.

However manual processing of the pressure transducer output signal into a flow rate or other data would be tedious and time consuming. For this reason, a processor 35 is provided to manipulate the pressure transducer output signal into a more useful form. The processor 35 includes an analog to digital converter 36, a central processing unit 37 and a digital to analog converter 38. The pressure transducer 30 output signal is input to the analog to digital converter 36. The analog to digital converter converts the pressure transducer output signal into a digital signal which is suitable to be input to the central processing unit 37. The central processing unit 37 is programmed to convert the digitized pressure signal into a flow rate or other data and to output the data to the digital to analog converter 38. The digital to analog converter converts the digital flow rate signal into an analog signal which is suitable to be input to a remote printer 40 to provide a histogram of the flow rate and/or other data.

A flow chart of a program for converting the air pressure into a flow rate is given in FIG. 5. The preferred processing technique of FIG. 5 employs a central processing unit 37 which has an internal clock which can generate a read signal at set intervals $\Delta t$ such as the microcomputer sold under the trade designation Intel 8051. The processing unit is programmed to await the signal from the internal clock to begin the portion of the program wherein the pressure signal is read and processed into the flow rate. After initializing all registers, the first step in this portion of the program would be to generate an enable signal to be carried by an enable line 41 to the analog to digital converter 36. The analog to digital converter 36 converts the pressure signal from the transducer 30 into a digital signal which is carried by a data bus 42 to the central processing unit 37 where it is read.

The central processing unit 37 then converts the pressure signal into a volume of urine within the collector 12 and into a flow rate out of the collector 12. If a table compiled as previously explained is used, the experimentally determined pressure, accumulated volume, and flow rate out data is stored in associated memory addresses. The processor compares the input pressure value to the stored experimental pressure values and stores the memory address of the experimental pressure value which is closest to the input pressure value. The processor then goes to the associated accumulated volume and flow rate out addresses to determine the accumulated volume of urine within the collector 12 and the flow rate out of the collector 12, respectively. These simple processing techniques are symbolized by the box labeled TABLE in the flow chart in FIG. 5.

Returning to the main portion of the flow chart in FIG. 5, the accumulated volume and flow rate out are stored. Next, the average flow rate out for the time interval since the last pressure reading is calculated. This is done simply by adding the last obtained flow rate out to the most recently obtained flow rate out and dividing the sum by two. The average flow rate out is then stored. The next step of the program is to calculate the average rate of change of the accumulated volume of urine in the collector 12 over the time interval since the last pressure reading. This is done by subtracting the last obtained volume from the most currently obtained volume and dividing the difference by the time interval. Adding the average rate of change of the accumulated volume of urine in the collector 12 to the average flow rate out yields the average flow rate in for the time interval between the two most current readings of the air pressure. The average flow rate in and the time of the reading are then stored.

The average flow in and the time of the most current reading are displayed via the digital to analog converter 38. The central processing unit 37 generates an enable signal which is carried by an enable line 44 to the digital to analog converter 38. The digital to analog converter 38 then reads the digitized flow in and time signals from the data bus 42 and converts them into analog signals to be output to the remote printer 40. Preferably, the output of the remote printer 40 is in the form of a graph with the vertical axis as the average flow in and the horizontal axis as time.

After the display step, the program checks to see if the average flow rate in equals 0. If the flow rate in equals 0, that is, if there is no flow in, it may indicate that urination has ceased so that it is desirable to stop processing. To this end, a no flow timer is incremented with Δt. If the elapsed time of the no flow timer has exceeded a certain maximum period, then the program stops. If it has not exceeded that period, the processor returns to await another read signal from the clock. This way, a momentary interruption in urine flow will not result in stopping the processor. If the average flow rate in is not equal to 0, the no flow timer is initialized and the processor returns to await another read signal from the clock.

The resulting flow rate data could be processed to yield other data. For example, the flow rate in and time data could be integrated to yield the total volume of urine voided by the patient. Also, the starting time of voiding could be subtracted from the ending time to yield the total time of voiding. Other quantities such as the peak flow, the time of the peak, and the average flow could also be determined and output.

A urine flow meter of the present invention has several advantages over prior art urine flow meters. First, the invention reduces the level of patient anxiety during a urine flow test. Since the patient is accustomed to voiding into a toilet, the patient will suffer less anxiety when voiding into the collector 12 held within the toilet 14 than would be the case were the patient to void into a separate receptacle of a prior art urine flow meter.

Second, little if any maintenance is required of a urine flow meter of the invention. A collector 12 for the invention can be inexpensively molded from a resin such as polyethylene so that it can be disposed of after each use. Furthermore, urine never contacts the nondisposable components of the invention such as the pressure transducer 30 so that they need not be cleaned after each use.

Additionally, the invention facilitates the taking of a urine sample. By disconnecting the pressure sender 28 from the pressure transducer 30, urine may be sucked from the neck portion 18 by a vacuum pump (not shown).

Numerous modifications and variations of the preferred embodiment will be apparent to those skilled in the art which will result in flow meters which embody the invention. Therefore, it is not intended that the invention be limited by the scope of the preferred embodiment described and illustrated herein, but by the claims which follow.

I claim:

1. A disposable collector to be used in a urine flow meter for measuring the flow rate of a stream of urine as it is voided into the collector, comprising:

a lower neck portion having an open upper end and a substantially closed lower portion, said lower portion having a first aperture formed therein which is sized and positioned so that a typical urine flow causes urine to accumulate in the neck portion above the first aperture until the pressure at the first aperture causes a urine flow out the neck portion equal to the urine flow into the collector;

an upper mouth portion having walls which slope downwardly and inwardly from an open upper end to an open lower end, said lower end of the mouth portion being coextensive with the upper end of the neck portion to funnel the stream of urine into the neck portion;

a pressure sender having a lower end in communication with the lower portion of the neck portion below the aperture and an upper end above the neck portion suitable for connection to a pressure transducer so that urine collected in the neck portion produces an air pressure in the pressure sender which is sensed by the pressure transducer; and wherein the collector is dimensioned to be supported within a toilet bowl so that urine collected in the neck portion drains from the aperture into the toilet bowl.

2. The collector of claim 1, further comprising means for inhibiting swirling of the urine in the neck portion.

3. The collector of claim 2, further comprising a second aperture smaller than the first aperture formed in the neck portion below the first aperture and above the lower end of the pressure sender, said second aperture having a tube downwardly depending therefrom on the exterior of the neck portion to lower the level of urine in the neck portion to below the first aperture by siphon action when there is no flow into the collector thereby reducing surface tension effects of the urine at the first aperture.

4. A collector for a urine flow meter in which a pressure transducer senses an air pressure within the collector which varies in accordance with the volume of urine in the collector, comprising:

a mouth portion dimensioned to fit within a toilet bowl and having walls which slope downwardly and inwardly from an open upper end to an open lower end;

a neck portion connected to the lower end of the mouth portion and extending downwardly therefrom, the neck portion having an open upper end and a substantially closed lower portion, a first aperture being formed in a sidewall of said lower portion;

a pressure sender having a lower end in communication with the lower portion of the neck portion and an upper end above the neck portion suitable for connection to the pressure transducer so that a urine flow entering the mouth portion accumulates in the neck portion and produces the air pressure within the pressure sender; and a second aperture smaller than the first aperture formed in the neck portion below the first aperture and above the lower end of the pressure sender and having a tube downwardly depending therefrom on the exterior of the neck portion to lower the level of urine to below the first aperture when there is no flow into the collector thereby reducing surface tension effects of the urine when it is at the level of the first aperture.

* * * * *